United States Patent [19]
Uhr et al.

[11] Patent Number: 5,925,675
[45] Date of Patent: Jul. 20, 1999

[54] N-SULFONYLIMINODITHIO COMPOUNDS USEFUL FOR IN PLANT AND MATERIAL PROTECTION

[75] Inventors: Hermann Uhr, Krefeld; Martin Kugler, Leichlingen; Heinrich Schrage, Krefeld, all of Germany

[73] Assignee: Bayer Aktiengesellschaft, Leverkusen, Germany

[21] Appl. No.: 09/011,724

[22] PCT Filed: Aug. 19, 1996

[86] PCT No.: PCT/EP96/03639

§ 371 Date: Feb. 18, 1998

§ 102(e) Date: Feb. 18, 1998

[87] PCT Pub. No.: WO97/08140

PCT Pub. Date: Mar. 6, 1997

[30] Foreign Application Priority Data

Aug. 31, 1995 [DE] Germany ............ 195 32 061

[51] Int. Cl.⁶ .......................... A01N 43/32; A01N 41/06
[52] U.S. Cl. .................. 514/508; 504/154; 504/160; 514/456; 558/2; 549/366
[58] Field of Search ............... 558/2; 549/366; 514/456, 508; 504/154, 160

[56] References Cited

U.S. PATENT DOCUMENTS 3,322,788  5/1967  Gompper et al. .................. 558/2

FOREIGN PATENT DOCUMENTS

A-112289  6/1984  European Pat. Off..
A-257069  6/1988  Germany.

OTHER PUBLICATIONS

Zeitschrift Fur Chemie, vol., 26, No. 6, Jun. 1986, Leipzig, DE pp. 204–205.

Chemische Bedrichte, vol. 99m No. 9, Sep. 1, 1966, Weinheim, DE, pp. 2885–2899.

Chemische Bedrichte, vol. 99m No. 9, Sep. 1, 1966, Weinheim, DE, pp. 2900–2904.

*Primary Examiner*—Peter O'Sullivan
*Attorney, Agent, or Firm*—Sprung Kramer Schaefer & Briscoe

[57] ABSTRACT

N-sulfonyliminodithio compounds have the formula (I), in which $R^1$ and $R^2$ stand for optionally substituted alkyl, alkenyl or alkinyl, and Ar stands for optionally substituted aryl; also disclosed are processes for preparing these compounds and their use for plant and material protection.

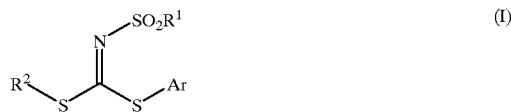

8 Claims, No Drawings

N-SULFONYLIMINODITHIO COMPOUNDS USEFUL FOR IN PLANT AND MATERIAL PROTECTION

The invention relates to new N-sulphonyliminodithio compounds, processes for their preparation, and use in plant and material protection.

N-sulphonyliminodialkylthio compounds of similar structure which are biologically inactive have already been described (R. Gompper, H. Haigele; Chem. Ber. 99, 2885 (1966).

Structurally similar N-arylsulphonyliminodithio compounds are likewise known, a biological action is not described (M. Hans, H. Dehne, R. Hartwig; Z. Chem. 26, 204 (1986).

Further N-arylsulphonyliminothiocarboxylic acid diesters are described as herbicide safeners (EP 112 289).

Surprisingly, it has now been found that the new N-sulphonyliminodithio compounds of the general formula (I)

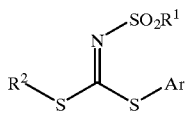

in which
R$^1$ and R$^2$ represent optionally substituted alkyl, alkenyl or alkinyl, and
Ar represents optionally substituted aryl are outstandingly suitable for the protection of plants and materials. Additionally, new processes for the preparation of N-sulphonyliminodithio compounds of the formula (I) have been found.

Formula (I) provides a general definition of the new N-sulphonyliminodithio compounds according to the invention. Preferred compounds of the formula (I) are those in which
R$^1$ and R$^2$ independently of one another represent straight-chain or branched alkyl having 1 is 10 carbon atoms, straight-chain or branched alkenyl having 2 to 10 carbon atoms or straight-chain or branched alkinyl having 2 to 10 carbon atoms, which in each case are optionally mono- to polysubstituted identically or differently by halogen, alkoxy having 1 to 6 carbon atoms, halogenoalkoxy having 1 to 6 carbon atoms and 1 to 9 identical or different halogen atoms, alkylthio having 1 to 6 carbon atoms, halogenoalkylthio having 1 to 6 carbon atoms and 1 to 9 identical or different halogen atoms, acyl having 1 to 6 carbon atoms, acyloxy having 1 to 6 carbon atoms, (alkoxy)-carbonyl having 1 to 6 carbon atoms, amino which is optionally identically or differently substituted by alkyl or aryl, optionally in each case substituted phenoxy, aryl, pyridyl or pyridyloxy, nitro or cyano, and
Ar represents aryl,
which is optionally mono- to pentasubstituted by halogen, alkyl having 1 to 10 carbon atoms, halogenoalkyl having 1 to 8 carbon atoms and 1 to 8 identical or different halogen atoms, alkoxy having 1 to 10 carbon atoms, halogenoalkoxy having 1 to 8 carbon atoms and 1 to 8 identical or different halogen atoms, alkylthio having 1 to 10 carbon atoms, halogenoalkylthio having 1 to 8 carbon atoms and 1 to 8 identical or different halogen atoms, amino, monoalkylamino with straight-chain or branched alkyl radicals having 1 to 6 carbon atoms, dialkylamino with identical or different, straight-chain or branched alkyl radicals each having 1 to 6 carbon atoms, cycloalkyl having 1 to 6 carbon atoms, methylenedioxy, difluoromethylenedioxy, chlorofluoromethylenedioxy, dichloromethylenedioxy, nitro or cyano.

Particularly preferred compounds of the formula (I) are those in which
R$^1$ and R$^2$ independently of one another represent straight-chain or branched alkyl having 1 to 8 carbon atoms, straight-chain or branched alkenyl having 2 to 8 carbon atoms or straight-chain or branched alkinyl having 2 to 8 carbon atoms, which in each case are optionally mono- to tetrasubstituted identically or differently by fluorine, chlorine, alkoxy having 1 to 5 carbon atoms, halogenoalkoxy having 1 to 5 carbon atoms and 1 to 5 fluorine and/or chlorine atoms, alylthio having 1 to 5 carbon atoms, halogenoalkylthio having 1 to 5 carbon atoms and 1 to 5 fluorine and/or chlorine atoms, acyl having 1 to 5 carbon atoms, acyloxy having 1 to 5 carbon atoms, alkoxycarbonyl having 1 to 5 carbon atoms, amino which is optionally identically or differently substituted by alkyl having 1 to 4 carbon atoms and/or phenyl, optionally in each case substituted phenoxy, aryl, pyridyl or pyridyloxy, nitro or cyano, and
Ar represents phenyl which is optionally mono- to tetrasubstituted by fluorine, chlorine, alkyl having 1 to 8 carbon atoms, halogenoalkyl having 1 to 6 carbon atoms and 1 to 6 fluorine and/or chlorine atoms, alkoxy having 1 to 8 carbon atoms, halogenoalkoxy having 1 to 6 carbon atoms and 1 to 6 fluorine and/or chlorine atoms, alkylthio having 1 to 8 carbon atoms, halogenoalkylthio having 1 to 6 carbon atoms and 1 to 6 fluorine and/or chlorine atoms, amino, monoalkylamino with alkyl radicals of 1 to 4 carbon atoms, dialkylamino with identical or different alkyl radicals in each case having 1 to 4 carbon atoms, cycloalkyl having 1 to 6 carbon atoms, methylenedioxy, difluoromethylenedioxy, chlorofluoromethylenedioxy, dichloromethylenedioxy, nitro or cyano.

Very particularly preferably, R$^1$ and R$^2$ represent methyl, ethyl, n- and i-propyl. n-, s-, i- and t-butyl, allyl and propargyl, which in each case are optionally substituted and by fluorine and/or chlorine, methoxy or methylthio.

It has been found that the N-sulphonyliminodithio compounds (I) are obtained when sulphonamides of the general formula (II)

where R$^1$ has the abovementioned meaning, are reacted within the presence of a base CS$_2$ and the resulting salt of the formula (III)

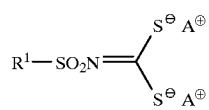

where R$^1$ has the abovementioned meaning and A$^\oplus$ represents a cation, such as, in particular, alkali metal, alkaline earth metal or trialkylammonium ion, is first made to react with a compound of the general formula (IV)

where $R^2$ has the meaning indicated above and X represents a leaving group, preferably chlorine, bromine, mesyl, tosyl, and the resulting salt of the formula (V),

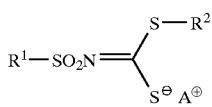
(V)

where $R^1$, $R^2$ and $A^\oplus$ have the meanings indicated above, is reacted, if appropriate in the presence of catalysts, with diazonium salt solutions from anilines of the formula (VI)

 (VI)

where Ar has the abovementioned meaning.

In the reaction sequence, the intermediates can either be isolated at any stage or the sequence can be carried out in a one-pot process without purification.

The alkylation step with (IV) and the reaction with the diazonium salt can also be exchanged in the synthesis sequence.

Additionally, the compounds of the general formula (I) are also obtained when compounds of the formula (VII),

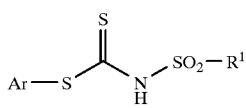
(VII)

in which $R^1$ and Ar have the abovementioned meaning, are reacted, optionally in the presence of a base, with alkylating agents of the general formula (IV).

In the preparation of the salts (III) from (II) using $CS_2$ in the presence of a base, the reaction can be carried out in various solvents depending on the base employed. The reaction is preferably carried out in water, alcohols, such as methanol, ethanol, butanol, butanol, ketones such as acetone or methyl ethyl ketone, ethers such as dioxane or THF, and also DMSO, DMPU, HMPT, DMF or NMP or mixtures of the solvents.

The bases used can be all customary bases. These preferably include tert-amines such as triethylamine and pyridine; alkali metal hydroxides such as sodium and potassium hydroxide; alkali metal carbonates and haydrogencarbonates such as potassium carbonate and sodium hydrogencarbonate; alkali metal and alkaline earth metal hydrides such as sodium hydride and calcium hydride; alkali metal alkoxides such as sodium ethoxide, potassium ethoxide, potassium methoxide, sodium ethoxide.

In general, 2 to 3 equivalents of base are employed, but larger excesses are also possible. The reaction temperatures for this reaction step can be varied over a wide range. In general, the reaction is carried out between $-30°$ C. and $+160°$ C., preferably between $-10°$ C. and $50°$ C. The reaction can be carried out both under atmospheric pressure, and under pressure in an autoclave.

For the reaction of the salt (III) with (IV) to give (V), the solvent can be changed. In this case, the solvents already mentioned above are possible for the sub-step. Preferably, however, the reaction is additionally carried out in the same solvent without isolation of the intermediates.

The temperatures of this sub-step can be varied within a relatively wide range. In general, the reaction is carried out between $-30°$ C. and $+100°$ C., preferably between $-10°$ C. and $50°$ C.

For the next sub-step, which consists in the reaction of (V) with diazonium salts, the solvent can likewise be changed, where, however, here too the already mentioned solvents can be employed. Preferably, V is not isolated, but the reaction is additionally carried out in the same solvent.

Preferably, a base and optionally a catalyst and then the diazonium salt solution are added to the solution. The bases used can be the bases already mentioned for the first sub-step, preferably alkali metal hydroxides such as, for example, potassium hydroxide or sodium hydroxide are employed. The catalysts employed can be all catalysts which promotes the replacement of the diazonium function by sulphur-containing radicals. Preferably, Cu(I) salts or copper powder are added. The temperature during the addition of the diazonium salt solution can be varied over a wide range. In general, the reaction is carried out between $-30°$ C. and $60°$ C., preferably between $-20°$ C. and $40°$ C.

The preparation of the diazonium salt solution from anilines is carried out according to literature methods.

The active compounds according to the invention have a strong microbicidal action and can be employed for the control of undesired micro-organisms, such as fungi and bacteria, in plant protection and in material protection.

Materials in the present connection are to be understood as meaning non-living materials which have been prepared for use in industry. For example, [lacuna] can be industrial materials which are to be protected from microbial change or destruction by active compounds according to the invention, adhesives, sizes, paper and card, textiles, leather, wood, paints and synthetic articles, cooling lubricants and other materials which can be attacked or decomposed by micro-organisms. In the context of the materials to be protected, parts of production plants, for example cooling water circulations which can be adversely affected by multiplication of micro-organisms may also be mentioned. In the context of the present invention, industrial materials which may be mentioned are preferably adhesives, sizes, papers and cards, leather, wood, paints, cooling lubricants and heat-transfer fluids.

Micro-organisms which may be mentioned which can cause degradation or alteration of the industrial materials are, for example, bacteria, fungi, yeasts, algae and slime organisms. Preferably, the active compounds or compositions according to the invention act against bacteria, fungi, in particular mould fungi, and against slime organisms and algae.

Micro-organisms of the following genera, for example, may be mentioned:

Alternaria, such as *Alternaria tenuis*,
Aspergillus, such as *Aspergillus niger*,
Chaetomium, such as *Chaetomium globosum*,
Coniophora, such as *Coniophora puetana*,
Lentinus, such as *Lentinus tigrinus*,
Penicillium, such as *Penicillium glaucum*,
Polyporus, such as *Polyporus versicolor*,
Aureobasidium, such as *Aureobasidium pullulans*,
Sclerophoma, such as *Sclerophoma pityophila*,
Trichoderma, such as *Trichoderma viride*,
Escherichia, such as *Escherichia coli*,
Pseudomonas, such as *Pseudomonas aeruginosa*,
Staphylococcus, such as *Staphylococcus aureus*.

Fungicidal agents in plant protection are employed for controlling Plasmodiophoro-mycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation:

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubense;*

Plasmopara species, such as, for example, *Plasmopara viticola;*

Peronospora species, such as, for example, *Peronospora pisi* or *Peronospora brassicae;*

Erysiphe species, such as, for example, *Erysiphe graminis;*

Sphaaerotheca species, such as, for example, *Sphaaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *Pyrenophora graminea* (conidia form: Drechslera, syn: Helminthosporium);

Cochliobolus species, such as, for example, *Cochliobolus sativus* (conidia form: Drechslera, syn: Helminthosporium);

Uromyces species, such as, for example, *Uromyces appendiculatus;*

Puccinia species, such as, for example, *Puccinia recondita;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Altemaria species, such as, for example, *Altemaria brassicae* and

Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

Depending on their particular physical and/or chemical properties, the active compounds of the formula (I) can be converted into customary formulations, such as solutions, emulsions, suspensions, powders, foams, pastes, granules, aerosols and very fine capsules in polymeric substances.

These formulations or compositions are produced in a known manner, for example by mixing the active compounds with extenders, that is liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. The following are mainly suitable as liquid solvents: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; liquefied gaseous extenders or carriers are to be understood as meaning liquids which are gaseous at ambient temperature and under atmospheric pressure, for example aerosol propellants, such as halogenated hydrocarbons as well as butane, propane, nitrogen and carbon dioxide; suitable solid carriers are: for example ground natural minerals, such as kaolins, clays, talc, chalk, quartz, attapulgite, montmorillonite or diatomaceous earth, and ground synthetic minerals, such as highly-disperse silica, alumina and silicates; suitable solid carriers for granules are: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; suitable emulsifying and/or foam forming agents are: for example non-ionic and anionic emulsifiers, such as polyoxyethylene fatty acid esters, polyoxyethylene fatty alcohol ethers, for example alkylaryl polyglycol ethers, alkylsulphonates, alkylsulphates, arylsulphonates as well as albumen hydrolysis products; suitable dispersants are: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, or else natural phospholipids, such as cephalins and lecithins and synthetic phospholipids can be used in the formulations. Other additives can be mineral and vegetable oils.

It is possible to use colourants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The activity and the spectrum of action of the active compounds of the formula (I) or the compositions, precursors or, very generally, formulations which can be prepared therefrom can be increased if other antimicrobially active compounds, fungicides, bactericides, herbicides, insecticides or other active compounds for increasing the spectrum of action or achieving particular effects such as, for example, the additional protection from insects, are optionally added. These mixtures may have a wider spectrum of action than the compounds according to the invention.

In many cases, synergistic effects are obtained here, i.e. the activity of the mixture is greater than the activity of the individual components. Particularly favourable mixing components are, for example, the following compounds:

Triazoles such as:

Amitrole, azocyclotin, BAS 480F, bitertanol, difenoconazole, fenbuconazole, fenchlorazole, fenethanil, fluquinconazole, flusilazole, flutriafol, imibenconazole, isozofos, myclobutanil, metconazole, epoxyconazole, paclobutrazol, penconazole, propioconazole, (±)-cis-1-(4-chlorophenyl)-2-(1H-1,2,4-triazol-1-yl)-cycloheptanol, tetraconazole, triadimefon, triadimenol, triapenthenol, triflumizole, triticonazole, uniconazole, and their metal salts and acid adducts.

Imidazoles such as:

Imazalil, pefurazoate, prochloraz, triflumizole, 2-(1-tert-butyl)-1-(2-chlorophenyl)-3-(1,2,4-triazol-1-yl)-propan-2-ol, thiazolecarboxanilides such as 2',6'-dibromo-2-methyl-4-trifluoromethoxy-4'-trifluoromethyl-1,3-thiazole-5-carboxanilide, 1-imidazolyl-1-(4'-chlorophenoxy)-3,3-dimethylbutan-2-one, and their metal salts and acid adducts;

Methyl(E)-2-[2-[6-(2-cyanophenoxy)pyrimidin-4-yloxy]phenyl]3-methoxyacrylate, methyl(E-2-[2-[6-(2-thioamidophenoxy)pyrimidin-4-yloxy]phenyl]-3-methoxyacrylate, methyl(E)-2-[2-[6-(2-fluorophenoxy)pyrimidin-4-yloxy]phenyl]-3-methoxyacrylate, methyl(E-2-[2-[6-(2,6-difluorophenoxy)pyrimidin-4-yloxy]phenyl]-3-methoxyacrylate, methyl(E-2-[2-[3-(pyrimidin-2-yloxy)phenoxy]phenyl]-3-methoxyacrylate, methyl(E)-2-[2-[3-(5-methylpyrimidin-2-yloxy)-phenoxy]phenyl]-3-methoxyacrylate, methyl(E)-2-[2-[3-(phenyl-sulphonyloxy)phenoxy]phenyl]-3-methoxyacrylate, methyl(E)-2-[2-[3-(4-nitrophenoxy)phenoxy]phenyl]-3-methoxyacrylate, methyl(E)-2-[2-phenoxyphenyl]-3-methoxyacrylate, methyl(E)-2-[2-(3,5-dimethylbenzoyl)pyrrol-1-yl]-3-methoxyacrylate, methyl(E)-2-[2-(3-methoxyphenoxy)phenyl]-3-methoxyacrylate, methyl(E)-2-[2-(2-phenylethen-1-yl)-phenyl]-3-methoxyacrylate, methyl(E)-2-[2-(3,5-dichlorophenoxy)-pyridin-3-yl]-3-methoxyacrylate, methyl(E)-2-(2-(3-(1,1,2,2-tetrafluoroethoxy)-phenoxy)phenyl)-3-methoxyacrylate, methyl(E)-2-(2-[3-(alpha-hydroxybenzyl)-phenoxy]phenyl)-3-methoxyacrylate, methyl(E)-2-(2-(4-phenoxypyridin-2-yloxy)-phenyl)-3-methoxyacrylate, methyl(E)-2-[2-(3-n-propyloxyphenoxy)phenyl]3-methoxyacrylate, methyl(E)-2-[2-(3-isopropyloxyphenoxy)phenyl]-3-methoxyacrylate, methyl (E)-2-[2-[3-(2-fluorophenoxy)phenoxy]phenyl]-3-methoxyacrylate, methyl(E)-2-[2-(3-ethoxyphenoxy)-phenyl]-3-methoxyacrylate, methyl(E)-2-[2-(4-tert.-butylpyridin-2-yloxy)phenyl]-3-methoxyacrylate, methyl(E)-2-[2-[3-(3-cyanophenoxy)phenoxy]phenyl]-3-methoxyacrylate, methyl(E)-2-[2-(3-methylpyridin-2-yloxymethyl)phenyl]-3-methoxyacrylate, methyl(E)-2-[2-[6-(2-methylphenoxy)pyrimidin-4-yloxy]phenyl]-3-methoxyacrylate, methyl(E)-2-[2-(5-bromopyridin-2-yloxymethyl)phenyl]-3-methoxyacrylatemethyl(E)-2-[2-(3-(3-iodopyridin-2-yloxy)phenoxy)phenyl]-3-methoxyacrylate, methyl(E)-2-[2-[6-(2-chloropyridin-3-yloxy)pyrimidin-4-yloxy]phenyl]-3-methoxyacrylate, (E),(E)methyl-2-[2-(5,6-dimethylpyrazin-2-ylmethyloximinomethyl)-phenyl]-3-methoxyacrylate, (E)-methyl-2-{2-[6-(6-methylpyridin-2-yloxy)pyrimidin-4-yloxy]phenyl }-3-methoxyacrylate, (E),(E)methyl-2-{2-(3-methoxyphenyl)methyloximinomethyl]phenyl}-3-methoxyacrylate, (E)-methyl-2-{2-(6-(2-azidophenoxy)-pyrimidin-4-yloxy]phenyl}3-methoxyacrylate, (E),(E)methyl-2-{2-[6-phenylpyrimidin-4-yl)-methyloximinomethyl]phenyl}-3-methoxyacrylate, (E),(E)methyl-2-{2-[(4-chlorophenyl)-methyloximinomethyl]phenyl}-3-methoxyacrylate, (E)methyl-2-{2-[6-(2-n-propylphenoxy)-1,3,5-triazin-4-yloxy]phenyl}-3-methoxyacrylate, (E),(E)methyl-2-{2-[(3-nitrophenyl)methyloximinomethyl]phenyl}-3-methoxyacrylate;

Succinate dehydrogenase inhibitors such as:

Fenfuram, furcarbanil, cyclafluramid, furmecyclox, seedvax, metsulfovax, pyrocarbolid, oxycarboxin, shirlan, mebenil (mepronil), benodanil, flutolanil (Moncut);

naphthalene derivatives such as terbinafine, naftifine, butenafine, 3-chloro-7-(2-aza-2,7,7-trimethyl-oct-3-en-5-ine);

sulphenamides such as dichlofluanid, tolylfluanid, folpet, fluorfolpet; captan, captofol;

benzimidazoles such as carbendazim, benomyl, furathiocarb, fuberidazole, thiophonatemethyl, thiabendazole or their salts;

morpholine derivatives such as tridemorph, fenpropimorph, falimorph, dimethomorph, dodemorph, aldimorph, fenpropidin and their arylsulphonyl salts, such as, for example, p-toluenesulphonic acid and p-dodecylphenyl-sulphonic acid;

dithiocarbamates, cufraneb, ferbam, mancopper, mancozeb, maneb, metam, metiram, thiram zeneb, ziram;

benzothioazoles such as 2-mercaptobenzothiazole;

benzamides such as 2,6-dichloro-N-(4-trifluoromethylbenzyl)-benzamide;

boron compounds such as boric acid, boric acid esters, borax;

formaldehyde and formaldehyde-cleaving compounds such as benzyl alcohol mono-(poly)-hemiformal, oxazolidines, hexa-hydro-S-triazines, N-methylolchloroacetamide, paraformadehyde, nitropyrin, oxolinic acid, tecloftalam;

tris-N-(cyclohexyldiazeniumdioxy)-aluminium, N-(cyclo-hexyldiazeniumdioxy)tributyltin or K salts, bis-N-(cyclohexyldiazeniumdioxy)-copper;

N-methylisothiazolin-3-one, 5-chloro-N-methylisothiazolin-3-one, 4,5-dichloro-N-octyl-isothiazolin-3-one, N-octyl-isothiazolin-3-one, 4,5-trimethylene-isothiazolinones, 4,5-benzisothiazolinones, N-methylolchloroacetamide;

aldehydes such as cinnamaldehyde, formaldehyde, glutaraldehyde, β-bromocinnamaldehyde; thiocyanates such as thiocyanatomethylthiobenzothiazole, methylene bisthiocyanate, etc.; quaternary ammonium compounds such as benzyldimethyltetradecylammonium chloride, benzyldimethyldodecylammonium chloride, didecyldimethaylammonium chloride;

iodine derivatives such as diiodomethyl-p-tolylsulphone, 3-iodo-2-propinyl alcohol, 4-chlorophenyl-3-iodopropargyl formal, 3-bromo-2,3-diiodo-2-propenylethyl carbamate, 2,3,3-triiodoallyl alcohol, 3-bromo-2,3-diiodo-2-propenyl alcohol, 3-iodo-2-propinyl-n-butyl carbamate, 3-iodo-2-propinyl-n-hexyl carbamate, 3-iodo-2-propinyl-cyclohexylcarbamate, 3-iodo-2-propinyl-phenyl carbamate;

phenol derivatives such as tribromophenol, tetrachlorophenol, 3-methyl-4-chlorophenol, 3,5-dimethyl-4-chlorophenol, phenoxyethanol, dichlorophen, o-phenylphenol, m-phenylphenol, p-phenylphenol, 2-benzyl-4-chlorophenol and their alkali metal and alkaline earth metal salts;

microbicides having an activated halogen group, such as chloroacetamide, bronopol, bronidox, tectamers such as 2-bromo-2-nitro-1,3-propanediol, 2-bromo-4'-hydroxyacetophenone, 2,2-dibromo-3-nitrile-propionamide, 1,2-dibromo-2,4-dicyanobutane, β-bromo-β-nitrostyrene;

pyridines such as 1-hydroxy-2-pyridinethione (and their Na, Fe, Mn, Zn salts), tetrachloro-4-methylsulphonylpyridine, pyrimethanol, mepanipyrim, dipyrithione, 1-hydroxy-4-methyl-6-(2,4,4-trimethylpentyl)-2(1H)-pyridine;

metal soaps such as tin, copper or zinc naphtenate, octoate, 2-ethylhexanoate, oleate, phosphate or benzoate;

metal salts such as copper hydroxycarbonate, sodium dichromate, potassium dichromate, potassium chromate, copper sulphate, copper chloride, copper borate, zinc fluorosilicate, copper fluorosilicate;

oxides such as tributyltin oxide, $Cu_2O$, CuO, ZnO;

dialkyldithiocarbamates such as Na and Zn salts of dialkyldithiocarbamates, tetramethylthiuram disulphide, potassium N-methyl-dithiocarbamate;

nitriles such as 2,4,5,6-tetrachloroisophthalodinitrile, disodium cyano-dithioimidocarbamate;

quinolines such as 8-hydroxyquinoline and their Cu salts;

mucochloric acid, 5-hydroxy-2(5H)-furanone;

4,5-dichlorodithiazolinone,4,5-benzodithiazolinone,4,5-trimethylenedithiazolinone,4,5-dichloro-(3H)-1,2-dithiol-3-one, 3,5-dimethyl-tetrahydro-1,3,5-thiadiazine-2-thione, N-(2-p-chlorobenzoylethyl)-hexaminium chloride, potassium N-hydroxymethyl-N'-methyl-dithiocarbamate, 2-oxo-2-(4-hydroxy-phenyl)acethydroximic acid chloride, phenyl 2-chloro-cyano-vinyl sulphone, phenyl 1,2-dichloro-2-cyano-vinyl sulphone, Ag, Zn or Cu-containing zeolites on their own or included in polymeric active compounds.

Very particularly preferred mixtures are those with azaconazole, bromuconazole, cyproconazole, dichlobutrazole, diniconazole, hexaconazole, metaconazole, penconazole, propioconazole, tebuconazole, methyl (E)-methoximino[α-(o-tolyloxy)-o-tolyl]acetate, methyl (E)-2-{2-[6-(2-cyanophenoxy)-pyrimidin-4-yl-oxy]phenyl}-3-methoxyacrylate, methfuroxam, carboxin, fenpiclonil, 4-(2,2-difluoro-1,3-benzodioxol-4-yl)-1H-pyrrole-3-carbonitrile, butenafine, imazalil, N-methyl-isothiazolin-3-one, 5-chloro-N-methylisothiazolin-3-one, N-octylisothiazolin-3-one, benzisothiazolinone, N-(2-hydroxypropyl)-amino-methanol, benzylalcohol (hemi)-formal, glutaraldehyde, omadine, dimethyl dicarbonate and/or 3-iodo-2-propinyl-n-butyl carbamate.

In addition, highly effective mixtures are also prepared using the following active compounds:

Fungicides:

Acypetacs, 2-aminobutane, ampropylfos, anilazine, benalaxyl, bupirimate, quinomethionate, chloroneb, chlozolinate, cymoxanil, dazomet, diclomezine, dichloran, diethofencarb, dimethirimol, diocab, dithianon, dodine, drazoxolon, edifenphos, ethirimol, etridiazole, fenarimol, fenitropan, fentin acetate, fentin hydroxide, ferimzone, fluazinam, fluromide, flusulphamide, flutriafol, fosetyl, fthalide, furalaxyl, guazatine, hymexazol, iprobenfos, iprodione, isoprothiolane, metalaxyl, methasulfocarb, nitrothalisopropyl, nuarimol, ofurace, oxadiyl, perflurazoate, pencycuron, phosdiphen, pimaricin, piperalin, procymidone, propamocarb, propineb, pyrazophos, pyrifenox, pyroquilon, quintozene, tar oils, tecnazene, thicyofen, thiophanate-methyl, tolclofos-methyl, triazoxide, trichlamide, tricyclazole, triforine, vinclozolin.

Insecticides:

Phosphoric acid esters such as azinphos-ethyl, azinphos-methyl, α-1(4-chlorophenyl)-4-(O-ethyl, S-propyl) phosphoryloxy-pyrazole, chlorpyrifos, coumaphos, demeton, demeton-S-methyl, diazinon, dichlorvos, dimethoate, ethoate, ethoprophos, etrimfos, fenitrothion, fenthion, heptenophas, parathion, parathion-methyl, phosalone, phoxim, pirimiphos-ethyl, pirimiphos-methyl, profenofos, prothiofos, sulfprofos, triazophos and trichlorphon;

carbamates such as aldicarb, bendiocarb, α-2-(1-methylpropyl)-phenyl methylcarbamate, butocarboxim, butoxycarboxim, carbaryl, carbofuran, carbosulfan, cloethocarb, isoprocarb, methomyl, oxamyl, pirimicarb, promecarb, propoxur and thiodicarb;

organosilicon compounds, preferably dimethyl(phenyl)silyl-methyl-3-phenoxybenzyl ethers such as dimethyl-(4-ethoxyphenyl)-silylmethyl-3-phenoxybenzyl ether or (dimethylphenyl)-silyl-methyl-2-phenoxy-6-pyridylmethyl ethers, such as, for example, dimethyl-(9-ethoxy-phenyl)-silylmethyl-2-phenoxy-6-pyridylmethyl ether or [(phenyl)-3-(3-phenoxyphenyl)-propyl] (dimethyl)-silanes such as, for example, (4-ethoxyphenyl)-[3-(4-fluoro-3-phenoxyphenyl-propyl]dimethyl-silane, silafluofen;

pyrethroids such as allethrin, alphamethrin, bioresmethrin, byfenthrin, cycloprothrin, cyfluthrin, decamethrin, cyhalothrin, cypermethrin, deltamethrin, alpha-cyano-3-phenyl-2-methylbenzyl 2,2-dimethyl-3-(2-chloro-2-trifluoro-methylvinyl)cyclopropane-carboxylate, fenpropathrin, fenfluthrin, fenvalerate, flucythrinate, flumethrin, fluvalinate, permethrin, resmethrin and tralomethrin;

nitroimines and nitromethylenes such as 1-[(6-chloro-3-pyridinyl)-methyl]-4,5-dihydro-N-nitro-1H-imidazol-2-amine (imidacloprid), N-[(6-chloro-3-pyridyl)methyl-]$N^2$-cyano-$N^1$-methylacetamide (NI-25);

abamectin, AC 303, 630, acephate, acrinathrin, alanycarb, aldoxycarb, aldrin, amitraz, azamethiphos, Bacillus thuringiensis, phosmet, phosphamidon, phosphine, prallethrin, propaphos, propetamphos, prothoate, pyraclofos, pyrethrins, pyridaben, pyridafenthion, pyrifoxyfen, quinalphos, RH-7988, rotenone, sodium fluoride, sodium hexafluorosilicate, sulfotep, sulfuryl fluoride, tar oils, teflubenzuron, tefluthrin, temephos, terbufos, tetrachlorvinphos, tetramethrin, O-2-tert-butyl-pyrimidin-5-yl-o-isopropyl-phosphorothiate, thiocyclam, thiofanox, thiometon, tralomethrin, triflumuron, trimethacarb, vamidothion, Verticillium Lacanii, XMC, xylylcarb, benfuracarb, bensultap, bifenthrin, bioallethrin, MERbioallethrin (S)-cyclopentenyl isomer, bromophos, bromophos-ethyl, buprofezin, cadusafos, calcium polysulphide, carbophenothion, cartap, quinomethionate, chlordane, chlorfenvinphos, chlorfluazuron, chlormephos, chloropicrin, chlorpyrifos, cyanophos, beta-cyfluthrin, alpha-cypermethrin, cyophenothrin, cyromazine, dazomet, DDT, demeton-S-methylsulphone, diafenthiuron, dialifos, dicrotophos, diflubenzuron, dinoseb, deoxabenzofos, diaxacarb, disulfoton, DNOC, empenthrin, endosulfan, EPN, esfenvalerate, ethiofencarb, ethion, etofenprox, fenobucarb, fenoxycarb, fensulfothion, fipronil, flucycloxuron, flufenprox, flufenoxuron, fonofos, formetanate, formothion, fosmethilan, furathiocarb, heptachlor, hexaflumuron, hydramethylnon, hydrogen cyanide, hydroprene, IPSP, isazofos, isofenphos, isoprothiolane, isoxathion, iodofenphos, kadethrin, lindane, malathion, mecarbam, mephosfolan, mercurous, chloride, metam, Metarthizium, aniospliae, methacrifos, methamidophos, methidathion, methiocarb, methoprene, methoxychlor, methyl isothiocyanate, metholcarb, mevinphos, monocrotophos, naled, neodiprion sertifer NPV, nicotine, omethoate, oxydemeton-methyl, pentachlorophenol, petroleum oils, phenothrin, phenthoate, phorate;

Molluscicides:

Fentin acetate, metaldehyde, methiocarb, niclosamide, thiodicarb, trimethacarb.

Algicides:

Copper sulphate, dichlorophen, endothal, fentin acetate, quinoclamine.

Herbicides

Acetochlor, acifluorfen, aclonifen, acrolein, alachlor, alloxydim, ametryn, amidosulfuron, amitrole, ammonium sulfamate, anilofos, asulam atrazine, aziptrotryne, benazolin, benfluralin, benfuresate, bensulfuron, bensulfide, bentazone, benzofencap, benzthiazuron, bifenox, bilanafos, borax, dichlorprop, dichlorprop-P, diclofop, diethatyl, difenoxuron, difenzoquat, diflufenican, dimefuron, dimepiperate, dimethachlor, dimethametryn, dimethipin, dimethylarsinic acid, dinitramine, dinoseb, dinoseb, dinoseb acetate, dinoseb, bromacil, bromobutide, bromofenoxim, bromoxynil, butachlor, butamifos, fuenachlor, butralin, butylate, carbetamide, CGA 184927, chlormethoxyfen, chloramben, chlorbromuron, chlorbutam, chlorfurenol, chloridazon, chlorimuron, chlomitrofen, chloroacetic acid, achloropicrin, chlorotoluron, chloroxuron, chlorpropham, chlorsulfuron, chlorthal, chlorthiamid, cinmethylin, cinofulsuron, clethodim, clomazone, clomeprop, clopyralid, cyanamide, cyanazine, dinoseb acetate, dinoterb, diphenamid, dipropetryn, diquat, dithiopyr, diduron, DNOC, PPX-A 788, DPX-E96361, DSMA, eglinazine, endothal, EPTC, esprocarb, ethalfluralin, ethidimuron, ethofumesate, fenoxaprop, fenoxaprop-P, fenuron, flamprop, flamprop-M, flazasulfuron, fluazifop, fluazifop-P, fluchloralin, flumeturon, fluorocgycofen, fluoronitrofen, flupropanate, flurenol, fluridone, flurochloridone, fluoroxypyr, cycloate, cycloxydim, 2,4-D, daimuron, dalapon, dazomet, 2,4-DB, desmedipham, desmetryn, dicamba, dichlorbenil, isoproturon, isouron, isoxaben, isoxapyrifop, lactofen, lenacil, linuron, LS830556, MCPA, MCPA-thioethyl, MCPB, mecoprop, mecoprop-P, mefanacet, mefluidide, metam, metamitron, metazachlor, methabenzthiazuron, methazole, methoproptryne, methyldymron, methyl isothiocyanate, metobromuron, fomosafen, fosamine, furyloxyfen, glufosinate, glyphosate, haloxyfop, hexazinone, imazamethabenz, imazapyr, imazaquin, imazethapyr, ioxynil, isopropalin, propyzamide, prosulfocab, pyrazolynate, pyrazolsulfuron, pyrazoxyfen, pyributicarb, pyridate, quinclorac, quinmerac, quinocloamine, quizalofop, quzizalofop-P, S-23121, sethoxydim, sifuron, simazine, simetryn, SMY 1500, sodium chlorate, sulfometuron, tar oils, TCA, metolachlor, metoxuron, metribzin, metsulfuron, molinate, monalide, monolinuron, MSMA, naproanilide, napropamide, naptalam, neburon, nicosulfuron, nipyraclofen, norflurazon, orbencarb, oaryzalin, oxadiazon, oxyfluorfen, paraquat, pebulate, pendimethalin, pentachlorophenol, pentaochlor, petroleum oils, phenmedipham, picloram, piperophos, pretilachlor, primisulfuron, prodiamine, proglinazine, propmeton, prometryn, propachlor, tebutam, tebuthiuron, terbacil, terbumeton, terbuthylazine, terbutryn, thiazafluoron, thifensulfuron, thiobencarb, thiocarbazil, tioclorim, tralkoxydim, tri-allate, triasulfuron, tribenzuron, triclopyr, tridiphane, trietazine, trifluralin, IBI-C4874 vernolate, propanil, propaquizafop, propazine, propham.

The weight ratios of the active compounds in these active compound combinations can be varied within relatively wide ranges.

Preferably, the active compound combinations contain the active compound to 0.1 to 99.9%, in particular to 1 to 75%, particularly preferably 5 to 50%, the remainder to 100% being made up by one or more of the abovementioned mixture components.

The microbicidal compositions or concentrates used for the protection of the industrial materials contain the active compound or the active compound combination in any concentration of 0.01 and 95% by weight, in particular 0.1 to 60% by weight.

The application concentrations of the active compounds or of the active compound combinations to be used depend on the nature and the occurrence of the micro-organisms to be combated and on the composition of the material to be protected. The optimum use amount can be determined by test series. In general, the application concentrations are in the range from 0.001 to 5% by weight, preferably from 0.05 to 1.0% by weight, based on the material to be protected.

The active compounds or compositions according to the invention advantageously make it possible to replace the microbicidal compositions available until now by more effective and less toxic compositions. They show good stability and advantageously have a wide spectrum of action.

The following examples serve to illustrate the invention. The invention is not restricted to the examples.

PREPARATION EXAMPLES

Example 1

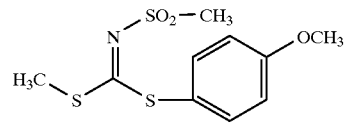

9.5 g (0.1 mol) of methylsulphonamide are initially introduced in DMF and treated with vigorous stirring with a solution of 4 g of NaOH in 6 ml of $H_2O$. 3.3 ml of $CS_2$ are added dropwise to the thick, white suspension. After a stirring time of 10 min, a solution of 2 g of NaOH in 3 ml of $H_2O$ is again added and 1.9 ml of $CS_2$ is then added. The process is repeated again after 10 min. 14.2 g (0.1 mol) of methyl iodide are added dropwise with cooling to the red solution obtained here. After an additional stirring time of about 2 h, 50 ml of 20% strength KOH and 7 g of Cu powder are added to the resulting suspension. After cooling to 0 to 5° C., the diazonium salt solution I (see below) is added dropwise. The mixture is additionally stirred for 2 h, the solid is filtered off with suction and washed with H₂O and the soluble constituents of the residue are taken up in ethyl acetate. After drying over Na₂SO₄, the solution is concentrated and chromatographed on silica gel (toluene).

Yield 6.5 g (22% of theory);

Physical constants see Table 1.

Diazonium salt solution I:

13.3 g (0.1 mol) of p-anisidene are initially introduced in 180 ml of H₂O and 25 ml of concentrated HCL at 2° C., treated dropwise with a solution of 7.3 g of NaNO₂ in 60 ml of H₂O and additionally stirred for 1 h.

The compounds of the formula (I) shown in Table 1 below are also prepared analogously to this example and corresponding to the above general details.

TABLE 1

(N-Sulphonyliminodithio compounds I)

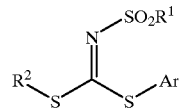

| Example No. | R¹ | R² | Ar | Physical constants |
|---|---|---|---|---|
| 1 | —CH₃ | —CH₃ | 4-OCH₃-C₆H₄ | 1H-NMR (CDCl₃) δ = 2.30 (3H, s); 3.19 (3H, s); 3.86 (3H, s); 6.95 (2H, s); 7.54 (2H, d) |
| 2 | —CH₃ | —CH₃ | 4-Cl-C₆H₄ | 1H-NMR (CDCl₃) δ = 2.34 (3H, s); 3.19 (3H, s); 7.48 (3H, d); 7.58 (2H, d) |
| 3 | —CH₃ | —CH₃ | 3,4-Cl₂-C₆H₃ | 1H-NMR (CDCl₃) δ = 2.37 (3H, s); 3.19 (3H, s); 7.50 (2H, s); 7.75 (1H, d) |
| 4 | —CH₃ | —CH₃ | 4-CH₃-C₆H₄ | 1H-NMR (CDCl₃) δ = 2.31 (3H, s); 2.43 (3H, s); 3.19 (3H, s); 7.26 (2H, d); 7.51 (2H, d) |
| 5 | —CH₃ | —CH₃ | C₆H₅ | 1H-NMR (CDCl₃) δ = 2.32 (3H, s); 3.19 (3H, s); 7.4–7.7 (5H, m) |
| 6 | —CH₃ | —CH₃ | 3-Cl-C₆H₄ | 1H-NMR (CDCl₃) δ = 2.35 (3H, s); 3.18 (3H, s); 7.30–7.67 (4H, m) |
| 7 | —CH₃ | —CH₃ | 2-Cl-C₆H₄ | 1H-NMR (CDCl₃) δ = 2.37 (3H, s); 3.19 (3H, s); 7.40/1H, m); 7.58 (2H, m); 7.75 (1H, m) |

TABLE 1-continued (N-Sulphonyliminodithio compounds I)

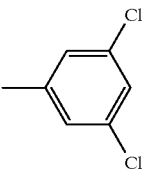

| Example No. | R¹ | R² | Ar | Physical constants |
|---|---|---|---|---|
| 8 | —CH$_3$ | —CH$_3$ | 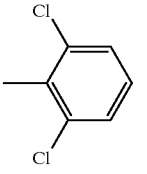 3,5-di-Cl-phenyl | 1H-NMR (CDCl$_3$) δ = 2.38 (3H, s); 3.18 (3H, s); 7.55 (3H) |
| 9 | —CH$_3$ | —CH$_3$ | 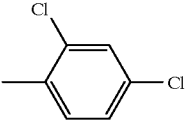 2,6-di-Cl-phenyl | 1H-NMR (CDCl$_3$) δ = 2.41 (3H, s); 3.19 (3H, s); 7.4–7.6 (3H, m) |
| 10 | —CH$_3$ | —CH$_3$ | 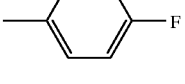 2,4-di-Cl-phenyl | 1H-NMR (CDCl$_3$) δ = 2.38 (3H, s); 3.19 (3H, s); 7.35 (1H, dd); 7.59 (1H, d); 7.65 (1H, d) |
| 11 | —CH$_3$ | —CH$_3$ | 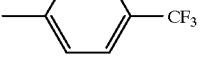 4-F-phenyl | 1H-NMR (CDCl$_3$) δ = 2.33 (3H, s); 3.19 (3H, s); 7.18 (2H, dd); 7.63 (2H, d); |
| 12 | —CH$_3$ | —CH$_3$ | 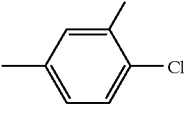 4-CF$_3$-phenyl | 1H-NMR (CDCl$_3$) δ = 2.36 (3H, s); 3.19 (3H, s); 7.69 (2H, d); 7.81 (2H, d); |
| 13 | —C$_2$H$_5$ | —CH$_3$ | 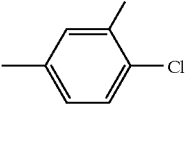 3,4-di-Cl-phenyl | 1H-NMR (CDCl$_3$) δ = 1.45 (3H, t); 2.36 (3H, s); 3.23 (2H, 7); 7.1–7.7 (3H, m). |
| 14 | —CF$_3$ | —CH$_3$ | 3,4-di-Cl-phenyl | |
| 15 | —CH$_2$SCH$_3$ | —CH$_3$ | 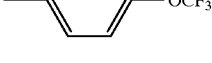 4-OCF$_3$-phenyl | |

TABLE 1-continued (N-Sulphonyliminodithio compounds I)

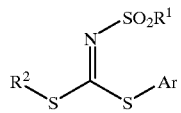

| Example No. | R₁ | R² | Ar | Physical constants |
|---|---|---|---|---|
| 16 | —C₄H₉ | —CH₃ | 4-CH₃-C₆H₄ | |
| 17 | —CH₃ | —CH₂C≡CH | 4-Cl-C₆H₄ | |
| 18 | —CH₂CH=CH₂ | —CH₃ | 3,4-(OCH₃)₂-C₆H₃ | |
| 19 | —CH₃ | —CH₂CH=CH₂ | 4-Cl-C₆H₄ | |
| 20 | —CH₃ | —CH₂C≡CH | 3,4-Cl₂-C₆H₃ | |
| 21 | —CH₃ | —CH₂—OCH₃ | 3,4-Cl₂-C₆H₃ | |
| 22 | —CH₃ | —CH₃ | 3,4-(O-CF₃-CF₃-O)-C₆H₃ | |
| 23 | —CH₃ | —CH₃ | 3,4-(O-CF₃-CFCl-O)-C₆H₃ | |

Use Examples

For demonstration of the activity against fungi, the minimum inhibitory concentrations (MIC) of compositions according to the invention are determined:

An agar which is prepared using malt extract is treated with active compounds according to the invention in concentrations of 0.1 mg/l to 5000 mg/l. After solidification of the agar, contamination with pure cultures of the test organisms shown in Table 1 is carried out. After storage at 28° C.

and 60 to 70% relative atmospheric humidity for 2 weeks, the MIC is determined. MIC is the lowest concentration of active compound at which no growth whatsoever by the microbial species used takes place, as is indicated in Table 2 below.

TABLE 2

Minimum inhibitory concentration (ppm) of compounds of the formula (I) according to the invention

| Example No. | 2 | 3 | Comparison compound* |
|---|---|---|---|
| Penicillium brevicaule | <40 | <40 | <400 |
| Chaetomium globosum | <40 | <40 | <400 |
| Aspergillus niger | 100 | >40 | <400 |

*from EP 112 289 p. 18 Example No. 3

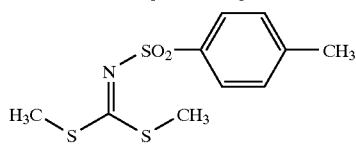

We claim:

1. Compounds of the general formula (I)

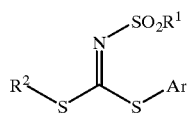

in which $R^1$ and $R^2$ represent optionally substituted alkyl, alkenyl or alkinyl, and Ar represents optionally substituted aryl.

2. Compounds of the formula (I) according to claim 1, in which $R^1$ and $R^2$ independently of one another represent straight-chain or branched alkyl having 1 is 10 carbon atoms, straight-chain or branched alkenyl having 2 to 10 carbon atoms or straight-chain or branched alkinyl having 2 to 10 carbon atoms, which in each case are optionally mono- to polysubstituted identically or differently by halogen, alkoxy having 1 to 6 carbon atoms, halogenoalkoxy having 1 to 6 carbon atoms and 1 to 9 identical or different halogen atoms, alkylthio having 1 to 6 carbon atoms, halogenoalkylthio having 1 to 6 carbon atoms and 1 to 9 identical or different halogen atoms, acyl having 1 to 6 carbon atoms, acyloxy having 1 to 6 carbon atoms, (alkoxy)-carbonyl having 1 to 6 carbon atoms, amino which is optionally identically or differently substituted by alkyl or aryl, optionally in each case substituted phenoxy, aryl, pyridyl or pyridyloxy, nitro or cyano, and Ar represents aryl, which is optionally mono- to pentasubstituted by halogen, alkyl having 1 to 10 carbon atoms, halogenoalkyl having 1 to 8 carbon atoms and 1 to 8 identical or different halogen atoms, alkoxy having 1 to 10 carbon atoms, halogenoalkoxy having 1 to 8 carbon atoms and 1 to 8 identical or different halogen atoms, alkylthio having 1 to 10 carbon atoms, halogenoalkylthio having 1 to 8 carbon atoms and 1 to 8 identical or different halogen atoms, amino, monoalkylamino with straight-chain or branched alkyl radicals having 1 to 6 carbon atoms, dialkylamino with identical or different, straight-chain or branched alkyl radicals each having 1 to 6 carbon atoms, cycloalkyl having 1 to 6 carbon atoms, methylenedioxy, difluoromethylenedioxy, chlorofluoromethylenedioxy, dichloromethylenedioxy, nitro or cyano.

3. Compounds of the formula (I), in which $R^1$ and $R^2$ independently of one another represent straight-chain or branched alkyl having 1 to 8 carbon atoms, straight-chain or branched alkenyl having 2 to 8 carbon atoms or straight-chain or branched alkinyl having 2 to 8 carbon atoms, which in each case are optionally mono- to tetrasubstituted identically or differently by fluorine, chlorine, alkoxy having 1 to 5 carbon atoms, halogenoalkoxy having 1 to 5 carbon atoms and 1 to 5 fluorine and/or chlorine atoms, alylthio having 1 to 5 carbon atoms, halogenoalkylthio having 1 to 5 carbon atoms and 1 to 5 fluorine and/or chlorine atoms, acyl having 1 to 5 carbon atoms, acyloxy having 1 to 5 carbon atoms, alkoxycarbonyl having 1 to 5 carbon atoms, amino which is optionally identically or differently substituted by alkyl having 1 to 4 carbon atoms and/or phenyl, optionally in each case substituted phenoxy, aryl, pyridyl or pyridyloxy, nitro or cyano, and Ar represents phenyl which is optionally mono- to tetrasubstituted by fluorine, chlorine, alkyl having 1 to 8 carbon atoms, halogenoalkyl having 1 to 6 carbon atoms and 1 to 6 fluorine and/or chlorine atoms, alkoxy having 1 to 8 carbon atoms, halogenoalkoxy having 1 to 6 carbon atoms and 1 to 6 fluorine and/or chlorine atoms, alkylthio having 1 to 8 carbon atoms, halogenoalkylthio having 1 to 6 carbon atoms and 1 to 6 fluorine and/or chlorine atoms, amino, monoalkylamino with alkyl radicals of 1 to 4 carbon atoms, dialkylamino with identical or different alkyl radicals in each case having 1 to 4 carbon atoms, cycloalkyl having 1 to 6 carbon atoms, methylenedioxy, difluoromethylenedioxy, chlorofluoromethylenedioxy, dichloromethylenedioxy, nitro or cyano.

4. A pesticidal composition comprising at least one compound of the formula (I) according to claim 1.

5. A method for combating pests, comprising allowing compounds of the formula (I) according to claim 1 to act on pests and/or their habitat.

6. Process for the preparation of pesticides, comprising mixing compounds of the formula (I) according to claim 1 with extenders and/or surface-active agents.

7. Process for the preparation of compounds of the formula (I) according to claim 1, comprising a) reacting sulphonamides of the general formula (II)

where $R^1$ has the meaning indicated in claim 1, with $CS_2$ in the presence of a base and the first reacting the resulting salt of the formula (III).

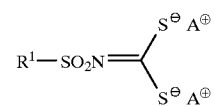

where $R^1$ has the abovementioned meaning and $A^\oplus$ represents a cation, with a compound of the general formula (IV)

$$R^2X \qquad (IV)$$

where $R^2$ has the meaning indicated in claim 1 and X represents a leaving group, and the reacting the resulting salt of the formula (V),

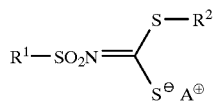 (V)

where $R^1$, $R^2$ and $A^\oplus$ have the meanings indicated above, if appropriate in the presence of catalysts, with diazonium salt solutions from anilines of the formula (VI)

$$H_2N\text{—}Ar \qquad (VI)$$

where Ar has the meaning mentioned in claim 1, or b) reacting compounds of the formula (VII),

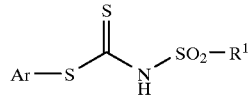 (VII)

in which $R^1$ and Ar have the meanings mentioned in claim 1, if appropriate in the presence of a base, with alkylating agents of the general formula (IV).

8. A method for combating pests in plant and material protection comprising allowing compounds of the formula (I) according to claim 1 to act on pests and/or their habitat.

* * * * *